(12) United States Patent
Bar-Tal

(10) Patent No.: US 9,629,570 B2
(45) Date of Patent: Apr. 25, 2017

(54) TRACKING OF CATHETER FROM INSERTION POINT TO HEART USING IMPEDANCE MEASUREMENTS

(71) Applicant: BIOSENSE WEBSTER (ISRAEL) LTD., Yokneam (IL)

(72) Inventor: Meir Bar-Tal, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 638 days.

(21) Appl. No.: 14/086,265

(22) Filed: Nov. 21, 2013

(65) Prior Publication Data

US 2015/0141798 A1   May 21, 2015

(51) Int. Cl.
| | |
|---|---|
| *A61B 5/06* | (2006.01) |
| *A61B 5/00* | (2006.01) |
| *G06T 19/00* | (2011.01) |
| *G01B 7/00* | (2006.01) |
| *G01B 7/004* | (2006.01) |
| *A61B 34/20* | (2016.01) |
| *G06F 19/00* | (2011.01) |

(52) U.S. Cl.
CPC .............. *A61B 5/063* (2013.01); *A61B 5/062* (2013.01); *A61B 5/6801* (2013.01); *A61B 5/6852* (2013.01); *A61B 5/7425* (2013.01); *A61B 34/20* (2016.02); *G01B 7/003* (2013.01); *G01B 7/004* (2013.01); *G06T 19/003* (2013.01); *A61B 2034/2051* (2016.02); *A61B 2560/0223* (2013.01); *G06F 19/3437* (2013.01); *G06T 2210/41* (2013.01)

(58) Field of Classification Search
CPC ......... A61B 34/20; A61B 5/062; A61B 5/063; A61B 5/6801; A61B 5/6852; A61B 5/7425
See application file for complete search history.

(56) References Cited

U.S. PATENT DOCUMENTS

| | | | |
|---|---|---|---|
| 7,536,218 B2 * | 5/2009 | Govari | A61B 5/0538 600/424 |
| 7,599,730 B2 | 10/2009 | Hunter | |
| 7,756,576 B2 | 7/2010 | Levin | |

(Continued)

OTHER PUBLICATIONS

EP Search Report EP 14 19 4002 Dated Feb. 2015.
(Continued)

*Primary Examiner* — Tse Chen
*Assistant Examiner* — Jason Ip
(74) *Attorney, Agent, or Firm* — Notaro, Michalos & Zaccaria P.C.

(57) ABSTRACT

A subject-specific skeletal model of a body is created, and an intended path of a catheter within the body is defined in the model. While the probe is inserted into the body electrical currents are passed through the body between at least one electrode in the probe and through respective electroconductive location pads that are disposed at a plurality of locations on the body surface along the intended path. Based on respective characteristics of the currents passing through the plurality of locations, position coordinates of the probe are iteratively determined. The actual path of the probe is tracked with reference to in the model using the iteratively determined position coordinates to determine whether the actual path corresponds to the intended path.

13 Claims, 7 Drawing Sheets

(56) References Cited

U.S. PATENT DOCUMENTS

| | | |
|---|---|---|
| 7,848,789 B2 | 12/2010 | Govari |
| 7,869,864 B2 | 1/2011 | Tseng |
| 8,456,182 B2 | 6/2013 | Bar-Tal |
| 2004/0068179 A1* | 4/2004 | Jutras .............. A61B 90/10 600/424 |
| 2005/0182295 A1 | 8/2005 | Soper et al. |
| 2006/0173251 A1 | 8/2006 | Govari |
| 2007/0016007 A1 | 1/2007 | Govari |
| 2007/0038078 A1 | 2/2007 | Osadchy |
| 2007/0060832 A1 | 3/2007 | Levin |
| 2008/0214931 A1 | 9/2008 | Dickfeld |
| 2008/0294258 A1 | 11/2008 | Revie |
| 2009/0203992 A1 | 8/2009 | Govari et al. |
| 2009/0221907 A1 | 9/2009 | Bar-Tal |
| 2009/0297001 A1 | 12/2009 | Markowitz |
| 2010/0079158 A1 | 4/2010 | Bar-Tal |
| 2011/0238083 A1 | 9/2011 | Moll |
| 2013/0006137 A1 | 1/2013 | Hauck et al. |
| 2013/0085380 A1 | 4/2013 | Velusamy |

OTHER PUBLICATIONS

Martin V. et al. MagnetoHemoDynamics in the Aorta and Electrocardiograms. Physics in Medicine and Biology. Phys. Med. Biol. 57 (2012) 3177-3195.

* cited by examiner

TRACKING OF CATHETER FROM INSERTION POINT TO HEART USING IMPEDANCE MEASUREMENTS

BACKGROUND OF THE INVENTION

Field of the Invention

This invention relates to sensing the position of an object placed within a living body. More particularly, this invention relates to improvements in a catheter tracking system using impedance measurements.

Description of the Related Art

The meanings of certain acronyms and abbreviations used herein are given in Table 1.

TABLE 1

Acronyms and Abbreviations

| ACL | Active Current Localization |
|---|---|
| EM | Electromagnetic |
| MRI | Magnetic Resonance Imaging |

A wide range of medical procedures involve placing objects, such as sensors, tubes, catheters, dispensing devices, and implants, within the body. Real-time imaging methods are often used to assist doctors in visualizing the object and its surroundings during these procedures. In most situations, however, real-time three-dimensional imaging is not possible or desirable. Instead, systems for obtaining real-time spatial coordinates of the internal object are often utilized.

U.S. Pat. No. 7,756,576 to Levin, whose disclosure is herein incorporated by reference, describes determining in near real-time the position of a probe placed within a living body. Electric currents are driven between one or more electrodes on the probe and electrodes placed on the body surface. The impedance between the probe and each of the body surface electrodes is measured, and three-dimensional position coordinates of the probe are determined based on the impedance measurements. Dynamic compensation is provided for changing impedance of the body surface and its interface with the electrodes.

U.S. Patent Application Publications 2006/0173251, of Govari et al., and 2007/0038078, of Osadchy, which are herein incorporated by reference, describe impedance-based methods for sensing the position of a probe by passing electrical currents through the body between an electrode on the probe and a plurality of locations on a surface of the body.

Impedance-based tracking systems have often been combined with another tracking system, e.g., an imaging modality such as fluoroscopy or magnetic resonance imaging, which is applied to the region of catheter insertion.

In another approach, U.S. Patent Application 2007/0016007, of Govari et al., whose disclosure is incorporated herein by reference, describes a hybrid magnetic-based and impedance-based position sensing system.

SUMMARY OF THE INVENTION

Rather than using two separate tracking systems, embodiments of the present invention rely on one enhanced impedance measuring system to track a catheter over a volume that extends from an insertion point to an operative region. A plurality of electroconductive body surface pads are attached to the patient in the region of insertion, which may typically be the groin or over the carotid arteries, in addition to pads in the region of the heart. The latter aid in tracking the catheter within the heart itself. All the pads are connected to an enhanced active current location (ACL) system, operated by a processor.

There is provided according to embodiments of the invention a method of catheterization, which is carried out by creating a subject-specific skeletal model of a body of a subject, defining in the model an intended path of a probe within the body that leads from a point of insertion of the probe to a target, and inserting the probe into the body. The method is further carried out by passing electrical currents through the body between at least one electrode in the probe and through respective electroconductive location pads that are disposed at a plurality of locations on a surface of the body, wherein the plurality of locations are distributed along the intended path of the probe. The method is further carried out by measuring respective characteristics of the currents passing through the plurality of locations, and while the probe is inserted, iteratively determining position coordinates of the probe responsively to the measured characteristics. The method is further carried out by tracking an actual path of the probe in the model using the iteratively determined position coordinates, and determining whether the actual path corresponds to the intended path.

According to an aspect of the method, the location pads are spaced apart at intervals between 20 and 40 mm.

According to another aspect of the method, operating volumes of immediately neighboring location pads overlap.

According to yet another aspect of the method, the at least one electrode includes a plurality of electrodes, and passing electrical currents includes passing each of the currents between one of the plurality of electrodes and one of the plurality of locations on the surface of the body.

According to still another aspect of the method, passing electrical currents includes affixing conductive pads in galvanic contact with the body at the plurality of locations, and passing electrical currents through the conductive pads.

According to another aspect of the method, at least one of the conductive pads is a multi-location pad having a plurality of location pad units.

According to an additional aspect of the method, tracking an actual path of the probe is performed exclusively using the iteratively determined position coordinates.

According to yet another aspect of the method, tracking an actual path of the probe is performed while avoiding imaging the body using another imaging modality.

According to one aspect of the method, the plurality of locations are relatively densely arranged near the target and more sparsely arranged elsewhere along the intended path of the probe.

Another aspect of the method the probe includes a magnetic sensor and is carried out by calculating additional position coordinates from signals produced by the magnetic sensor, determining a correlation between the position coordinates with the additional position coordinates, and refining the position coordinates responsively to the correlation.

According to a further aspect of the method, creating a subject-specific skeletal model includes applying a hand-held probe having a magnetic sensor to respective landmarks on the body, applying a magnetic field to the magnetic sensor, receiving signals from the magnetic sensor responsively to the magnetic field, computing respective positions of the landmarks responsively to the signals, and including the positions of the landmarks as reference locations in the model.

There is further provided according to embodiments of the invention an apparatus for position sensing, including a probe, having at least one probe electrode, which is adapted to be inserted into a body of a subject, a plurality of body surface electrodes, which are adapted to be fixed to a surface of the body at respective locations, and a controller, which is adapted to be coupled to the probe and to the body surface electrodes for passing electrical currents through the body between the at least one probe electrode and the plurality of body surface electrodes, and is operative to iteratively determine position coordinates of the probe by measuring respective characteristics of the currents passing through the plurality of body surface electrodes, and a processor, operative to perform the steps of: creating a subject-specific skeletal model of the body, in the model defining an intended path of the probe within the body that leads from a point of insertion of the probe to a target, tracking in the model an actual path of the probe during insertion thereof using the iteratively determined position coordinates, and determining whether the actual path corresponds to the intended path.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

System Description

Figure 1:
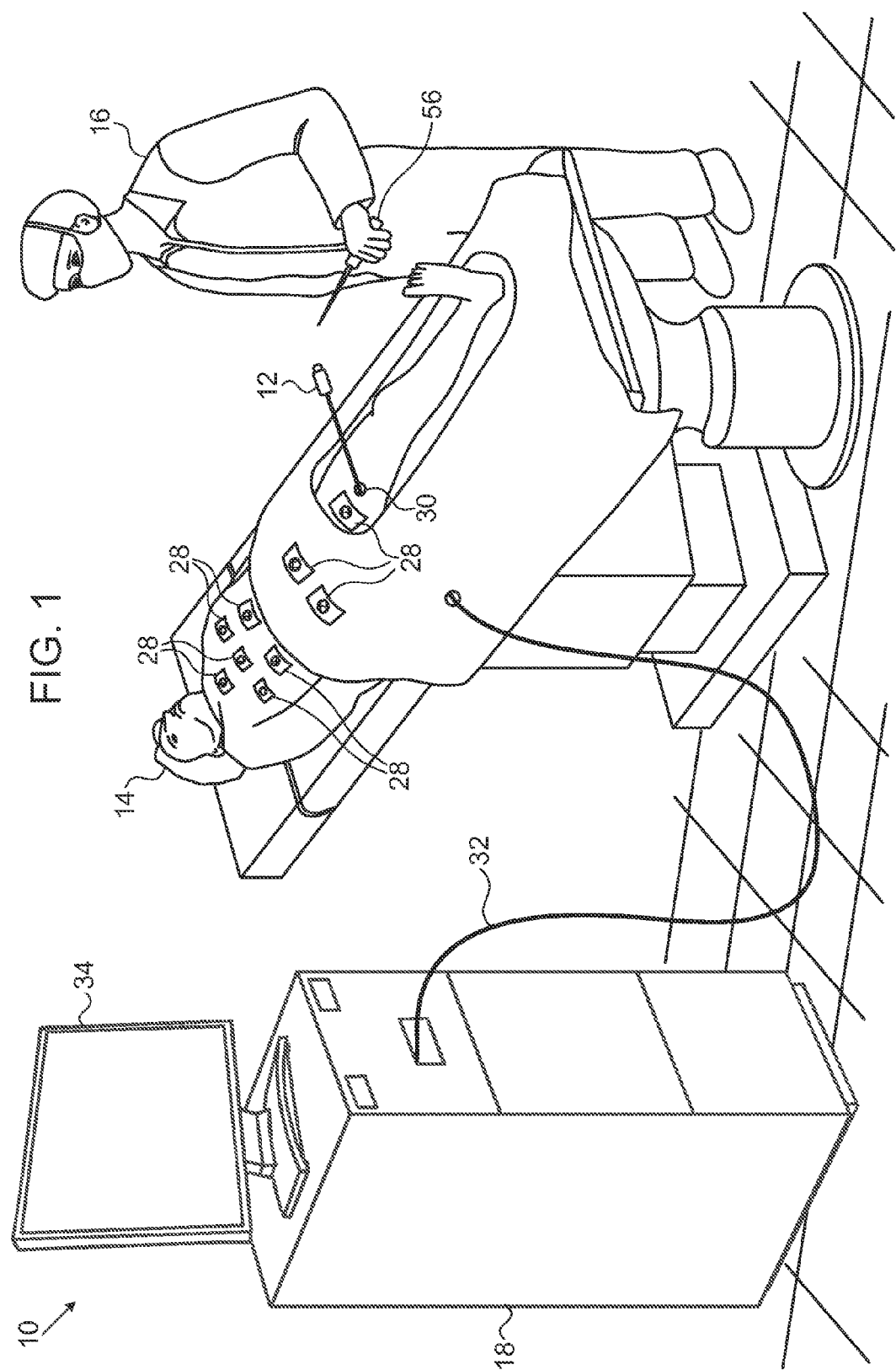
FIG. 1 is a schematic, pictorial illustration of a position tracking system, in accordance with an embodiment of the present invention.

Turning now to the drawings, Reference is initially made to FIG. 1, which is a schematic, pictorial illustration of a position tracking system 10, in accordance with an embodiment of the present invention. Impedance-based position tracking in the system 10 is performed by inserting a catheter 12 into an internal body cavity, such as a heart chamber of a subject 14. Typically, the catheter 12 is used for diagnostic or therapeutic treatment performed by medical practitioner 16, such as mapping electrical potentials in the heart or performing ablation of heart tissue. The catheter 12 or other intrabody device may alternatively be used for other purposes, by itself or in conjunction with other treatment devices. Processors and circuitry related to the medical procedure are found in a control unit 18.

Figure 2:
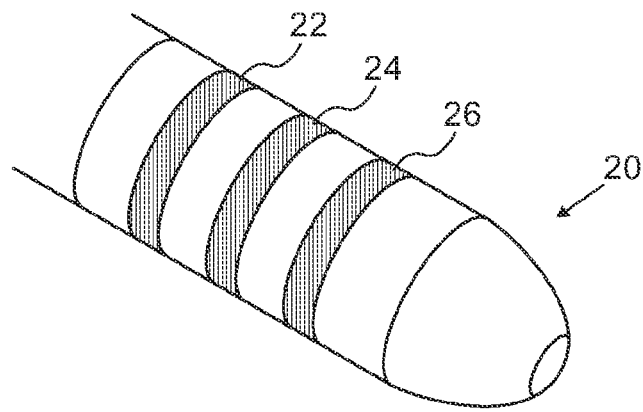
FIG. 2 is a schematic view of the distal segment of the catheter as shown in FIG. 1, in accordance with an embodiment of the invention.

Reference is now made to FIG. 2, which is a schematic view of the distal segment of the catheter 12 (FIG. 1), in accordance with an embodiment of the invention. Distal segment 20 comprises one or more electrodes 22, 24, 26 The electrode may be of any suitable shape and size, and may be used for other purposes, as well, such as for electrophysiological sensing or ablation. The electrodes are connected by to driver and measurement circuitry in the control unit 18 (FIG. 1).

Reverting to FIG. 1, a tracking sub-system within the system 10 is an active current localization subsystem, in which a plurality of body-surface electrodes, such as adhesive skin pads 28 are coupled to a body-surface, e.g., the skin of the subject 14. The pads 28 are in galvanic contact with the body surface of the subject 14, and receive body surface currents therefrom. The pads 28 may be placed at any convenient locations on the body-surface as appropriate to the medical procedure. Typically, the skin pads are spaced apart, but should be distributed generally along a path that extends from an insertion point 30 to a region over the target. For example, for cardiac applications, the pads 28 may be placed along the body of the subject 14 from the groin to the chest, where they are concentrated, i.e., increased in number and spaced more closely together, in order to provide enhanced resolution of the heart. In embodiments of the invention employing individual location pads, the location pads described in commonly assigned U.S. Patent Application Publication No. 2007/0060832, entitled "Detection of Skin Impedance", which is herein incorporated by reference, can be used as the pads 28.

In cardiac applications, positioning the pads 28 at 20-40 mm intervals along the intended course of the catheter during its introduction provides sufficient practical resolution to guide the operator. Optionally, location pads may be positioned along the course of vessels likely to cause unwanted deviation from the course, for example the renal arteries or veins, the great vessels of the neck, and the brachial arteries and veins as appropriate.

The pads 28 are also linked to the control unit 18, for example via a cable 32. The control unit 18 determines position coordinates of the catheter 12 inside the body of the subject 14 based on the currents measured between the catheter 12 and each of pads 28 and reported based on signals from the pads 28. The control unit 18 drives a monitor 34, which shows the catheter position inside the body of the subject 14. In cardiac applications, the catheter 12 may be used to generate an electroanatomic map of the heart, and the displayed position of the catheter 12 may be superimposed on the map or on another image of the heart.

The body surface electrodes of the ACL subsystem may be any type of body electrode known in the art, such as button electrodes, needle electrodes, subcutaneous probes, or pads as shown in FIG. 1.

Additionally or alternatively, one or more internal body electrodes (not shown) may be positioned in galvanic contact with, and inside, the body of the subject 14. The control unit 18 monitors the currents passing through the internal body-electrodes.

In any case, respective characteristics of currents passing between the catheter and the electrodes of the ACL subsystem are measured and the position coordinates of the catheter are determined responsively to the measured characteristics.

Details of the operation of the ACL subsystem are described in commonly assigned U.S. Pat. No. 7,869,865 to Govari et al. and U.S. Pat. No. 8,456,182 to Bar-Tal et al., which are herein incorporated by reference. In brief, a respective set of calibration currents is generated between the body-electrodes and the catheter at different positions in a region of interest. A respective relation is derived for each such region between the respective set of the calibration currents and the different positions, and is used in determining the location of an investigation tool in response to the different respective relations and investigation tool currents. There are calibration procedures and compensations for certain factors, e.g., location drift, respiration and heartbeat. One commercial product embodying the ACL subsystem is the CARTO® 3 System, available from Biosense Webster, Inc., 3333 Diamond Canyon Road, Diamond Bar, Calif. 91765. This system may be modified by those skilled in the art to embody the principles of the invention described herein.

Operation

Figure 3:
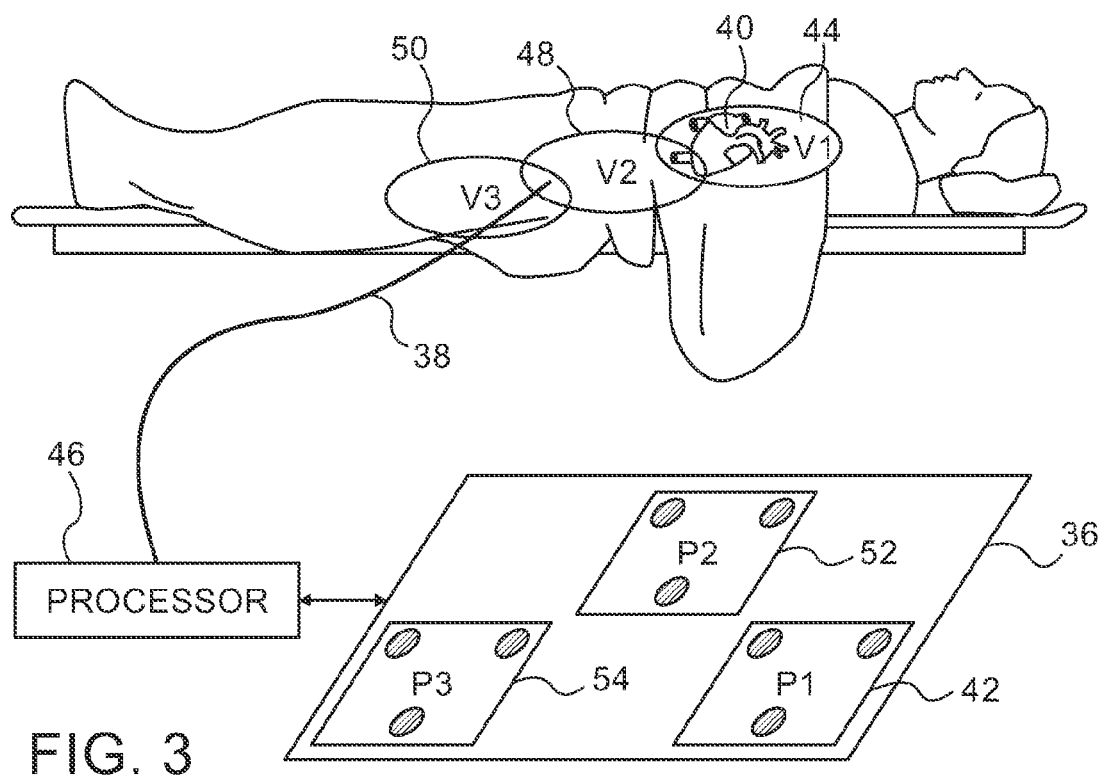
FIG. 3 is an enlarged view of a multi-location pad, in accordance with an embodiment of the invention.

Reference is now made to FIG. 3, which is a schematic view of a multi-location pad 36, in accordance with an embodiment of the invention. One way of tracking the distal end of a catheter 38 during its insertion employs the multi-location pad 36. The multi-location pad 36 is arranged relative to the patient, so that the useful operating volume of the multi-location pad 36 includes heart 40. Such a situation corresponds to pad unit P1 42, having operating volume V1 44, which includes heart 40. A processor 46 operates the multi-location pad 36. Operating volume V2 48 and operating volume V3 50 include regions along the path followed by the catheter as it is introduced into the patient. The operating volume V2 48 and operating volume V3 50 correspond to the coverage of pad unit P2 52 and pad unit P3 54, respectively.

Suitable electro-conductive elements for the multi-location pad 36 are disclosed in the above-noted U.S. Patent Application Publication No. 2007/0060832.

The pad units of the multi-location pad 36 are arranged to have overlapping operating volumes covering the expected path of the distal end of the catheter 38. While three volumes are shown in FIG. 3, any number of volumes may be employed. The pad units may also be physically connected together to form one large structure as shown in FIG. 3. Using the overlapping pad units, once an initial calibration has been performed to register the volumes V1 44, V2 48, V3 50, no further registration is required. Calibration can be accomplished by establishing known reference points and registering the reference points on an anatomical image model as described below. The location information provided by the ACL subsystem when configured according to FIG. 3 is sufficient to allow tracking of the catheter 38 during insertion without recourse to other imaging modalities, e.g., fluoroscopy or ultrasound.

These registration points are used to construct a patient-specific skeletal framework or model, using the capabilities of the above noted CARTO system. Once the model has been established, internal structures, such as blood vessels and the heart are added to the model and adjusted for accuracy according to whether the subject is male or female.

During insertion, the ACL subsystem may process data derived from selected ones of the pad units, particularly those whose operating volumes include or are relatively near the current location of the distal end of the catheter 38. More distant pad units are ignored or can be deactivated until the distal end arrives in or near their operating volumes. Alternatively, the pad units may be selectively connected and disconnected from the ACL subsystem during passage of the catheter 38 under control of the ACL subsystem processor.

First Alternate Embodiment

Referring again to FIG. 1, in order to further improve the accuracy of the ACL subsystem, an external handheld probe 56 containing an electromagnetic sensor is connected to the control unit 18. The system 10 for example the CARTO system, has well-known electromagnetic position tracking capabilities (EM tracking) that are based on readings from the magnetic sensor when the magnetic sensor is subjected to a magnetic field.

Figure 4:
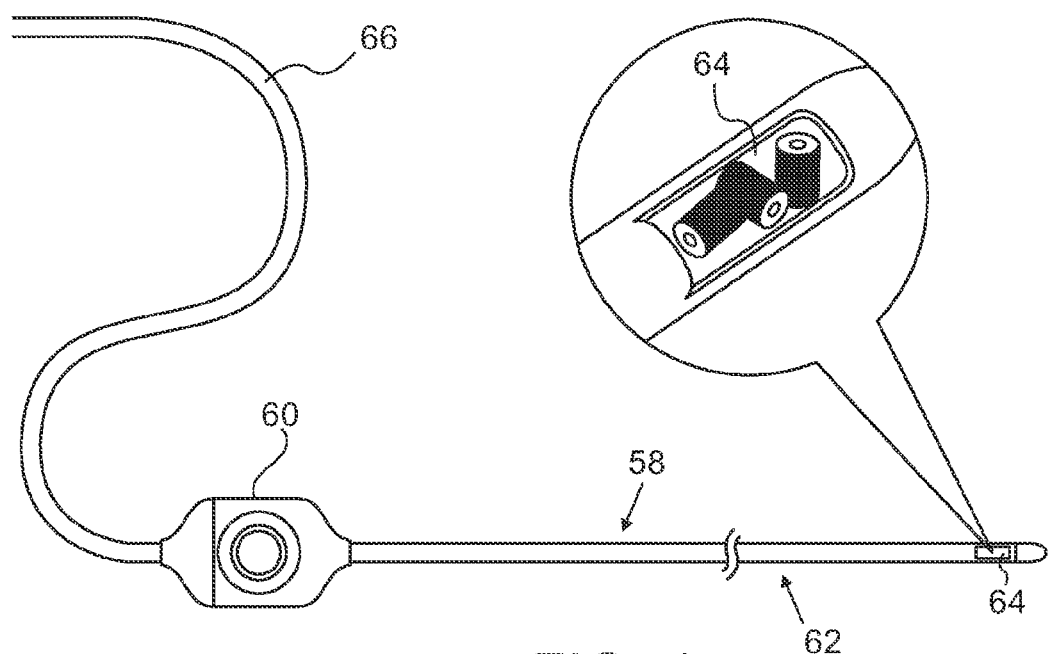
FIG. 4 illustrates a hand-held probe that may be used in the system shown in FIG. 1, in accordance with an embodiment of the present invention.

Reference is now made to FIG. 4, which is a schematic illustration of a hand-held probe 58 that may be used in the system shown in FIG. 1, in accordance with an embodiment of the invention. The probe 58 has a handle 60 at its proximal end to be grasped by a user. Distal portion 62 contains a magnetic sensor 64, which can be the sensor described in the above-noted U.S. Pat. No. 8,456,182 or in commonly assigned U.S. Patent Application Publication No. 2009/0221907, which is herein incorporated by reference. The probe 58 may communicate with control unit 18 wirelessly, or using a cable 66 as shown in FIG. 4.

The hand-held probe 56 is used to establish registration points corresponding to known patient-specific anatomical landmarks. For example, the hand-held probe 56 may be contacted to the skin of the subject 14 at particular registration points, such as the knees, ribs, or other specific parts of the body. The location of the magnetic sensor 64 at such points can be tracked and recorded by embodiments of the system 10 having electromagnetic tracking systems, such as the above-noted CARTO system. Techniques for establishing registration points using wireless position sensors that are taught in U.S. Patent Application Publication No. 2008/0294258, the disclosure of which is herein incorporated by reference. These techniques may be used, mutatis mutandis, to enhance the accuracy of the ACL subsystem by identifying to the ACL known patient-specific anatomic reference points.

Second Alternate Embodiment

Figure 5:
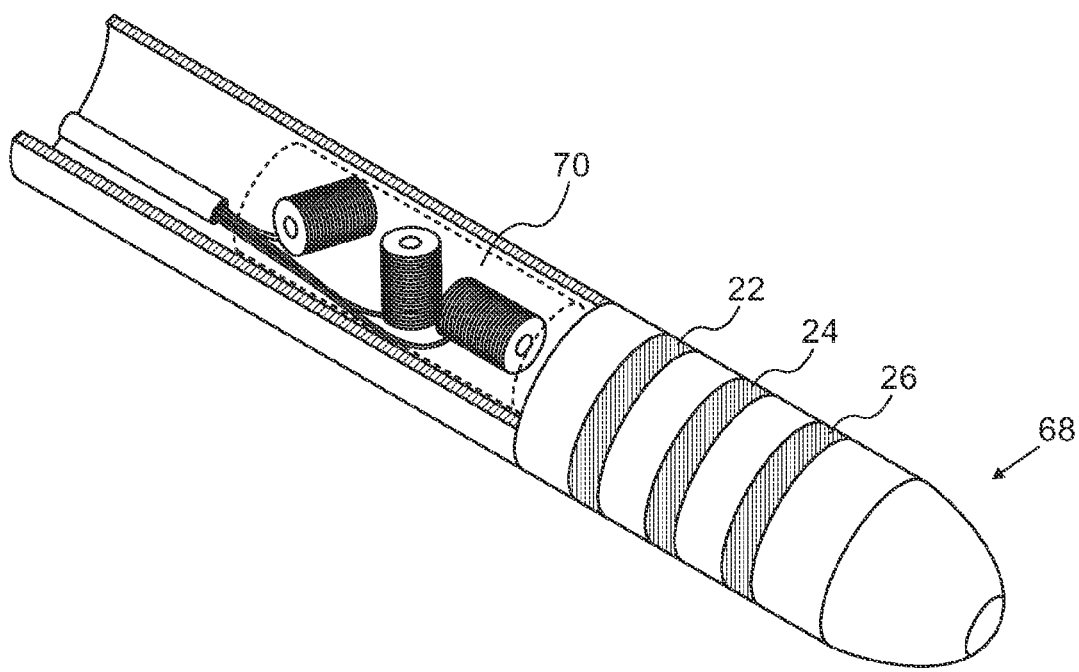
FIG. 5 is a schematic view of the distal segment of the catheter as shown in FIG. 1, in accordance with an alternate embodiment of the invention.

Reference is now made to FIG. 5, which is a schematic view of the distal segment of the catheter 12 (FIG. 1), in accordance with an alternate embodiment of the invention. Distal segment 68 now contains a magnetic sensor 70, which can be the sensor described in the above-noted U.S. Pat. No. 8,456,182.

The system 10 (FIG. 1), for example the CARTO system, has well-known electromagnetic position tracking capabilities (EM tracking) that are based on readings from the magnetic sensor 70. Accuracy of the enhanced ACL subsystem as described above is improved by correlating the impedance measurements taken from the multi-location pad 36 (FIG. 3) with additional location information provided by the magnetic sensor 70. The ACL subsystem may be calibrated or trained to conform to the position as computed from the data supplied by the magnetic sensor 70. The EM tracking system typically provides the catheter tip location and orientation with an accuracy of approximately 1 mm and 1 degree, respectively. Calibration of the ACL subsystem using the EM tracking system is described in the above-referenced U.S. Pat. No. 8,456,182. As in the previous embodiment, the accuracy of the system 10 in this embodiment is sufficient to enable introduction of the catheter 12 without recourse to other imaging modalities.

Third Alternate Embodiment

In this embodiment, the multi-location pad 36 shown in FIG. 3 is omitted. Instead, individual pads are placed on the body surface as shown in FIG. 1. The pads 28 are distributed relatively sparsely over the insertion region, where location measurements computed by the impedances are less exacting. The pads are relatively more numerous and densely arranged in the region of the heart, where accuracy is more important. For example, a pad density over the heart of between 2 and 3 times the pad density away from the heart is suitable.

Example

Figure 6:
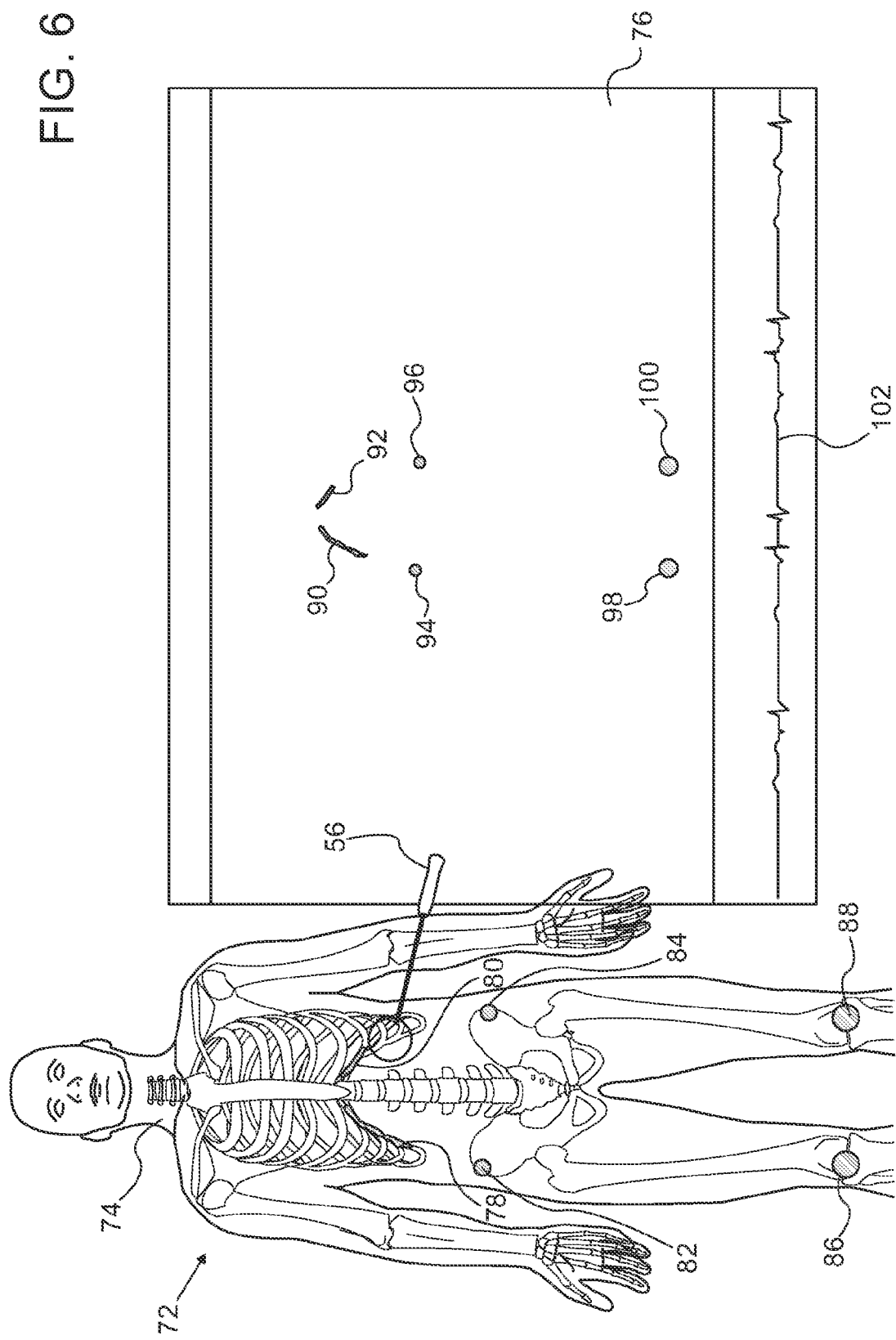
FIG. 6, which is a composite schematic of a skeletal model of a subject of a screen display, in accordance with an embodiment of the invention.

Reference is now made to FIG. 6, which is a composite schematic of a skeletal model 72 of a subject 74 and a screen display 76, which have been generated in accordance with an embodiment of the invention. The display 76 is connected to the ACL subsystem. However, the location pads have been omitted for clarity. The hand-held probe 56 has registered a number of anatomical landmarks, i.e., right costal margin 78, left costal margin 80, right anterior iliac spine 82, left anterior iliac spine 84, right patella 86 and left patella 88. These landmarks correspond to graphical indications 90, 92, 94, 96, 98, 100, respectively on the display 76. The landmarks shown are representative; others may be added as appropriate for a particular medical procedure. An electrocardiographic tracing 102 appears in the lower portion of a display 104.

Figure 7:
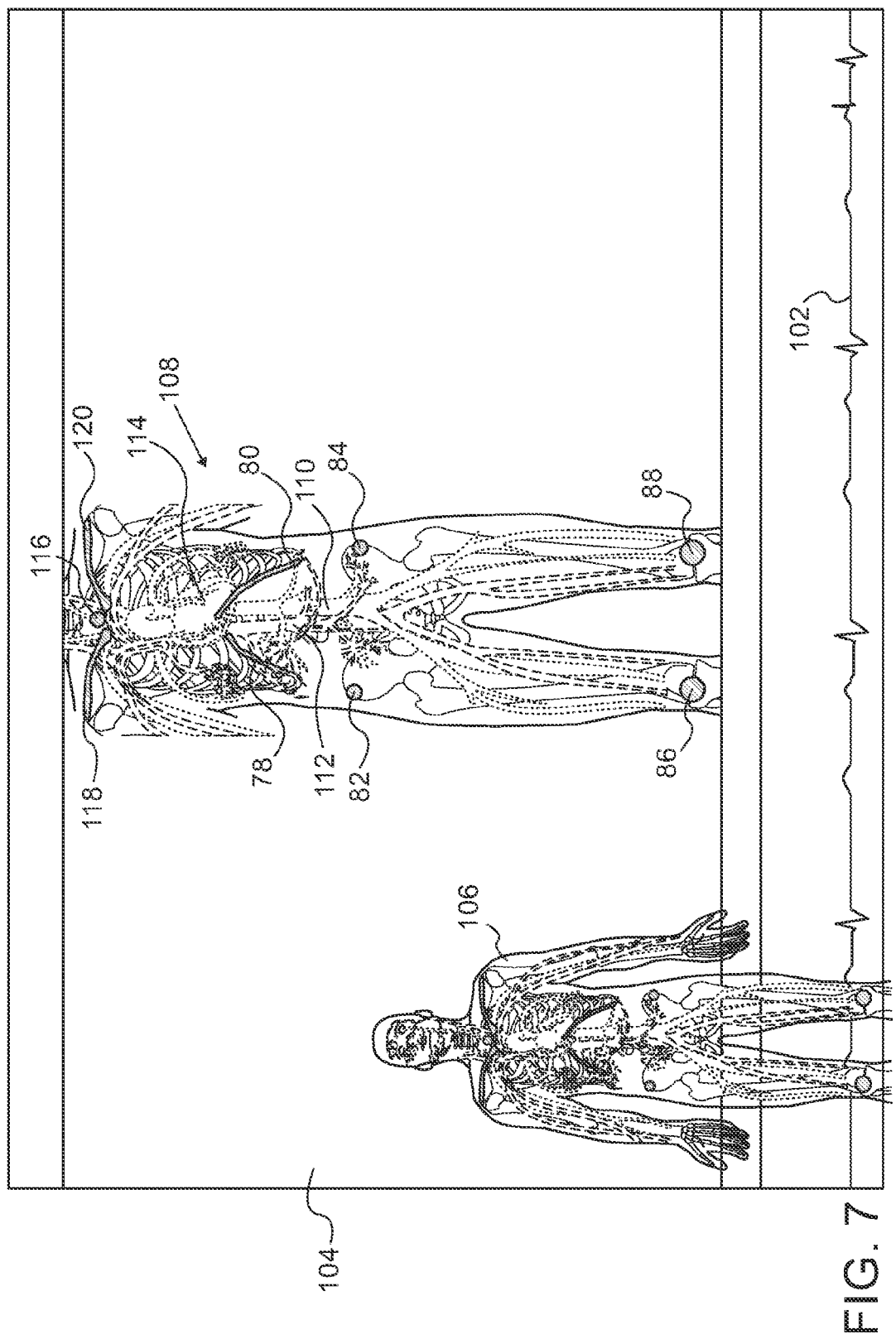
FIG. 7 is a composite illustration that includes a screen display of a skeletal model, in accordance with an embodiment of the invention.

Reference is now made to FIG. 7, which is a composite illustration that includes a screen display 104 of a skeletal model, in accordance with an embodiment of the invention. Internal anatomic structures taken from a reference skeletal model 106 have been mapped onto a patient-specific model 108 of the subject 74 (FIG. 6). Shown inter alia on the image model 108 are aorta 110, inferior vena cava 112 and heart 114. Additional anatomical landmarks have been provided: suprasternal notch 116 and clavicles 118, 120.

Figure 8:
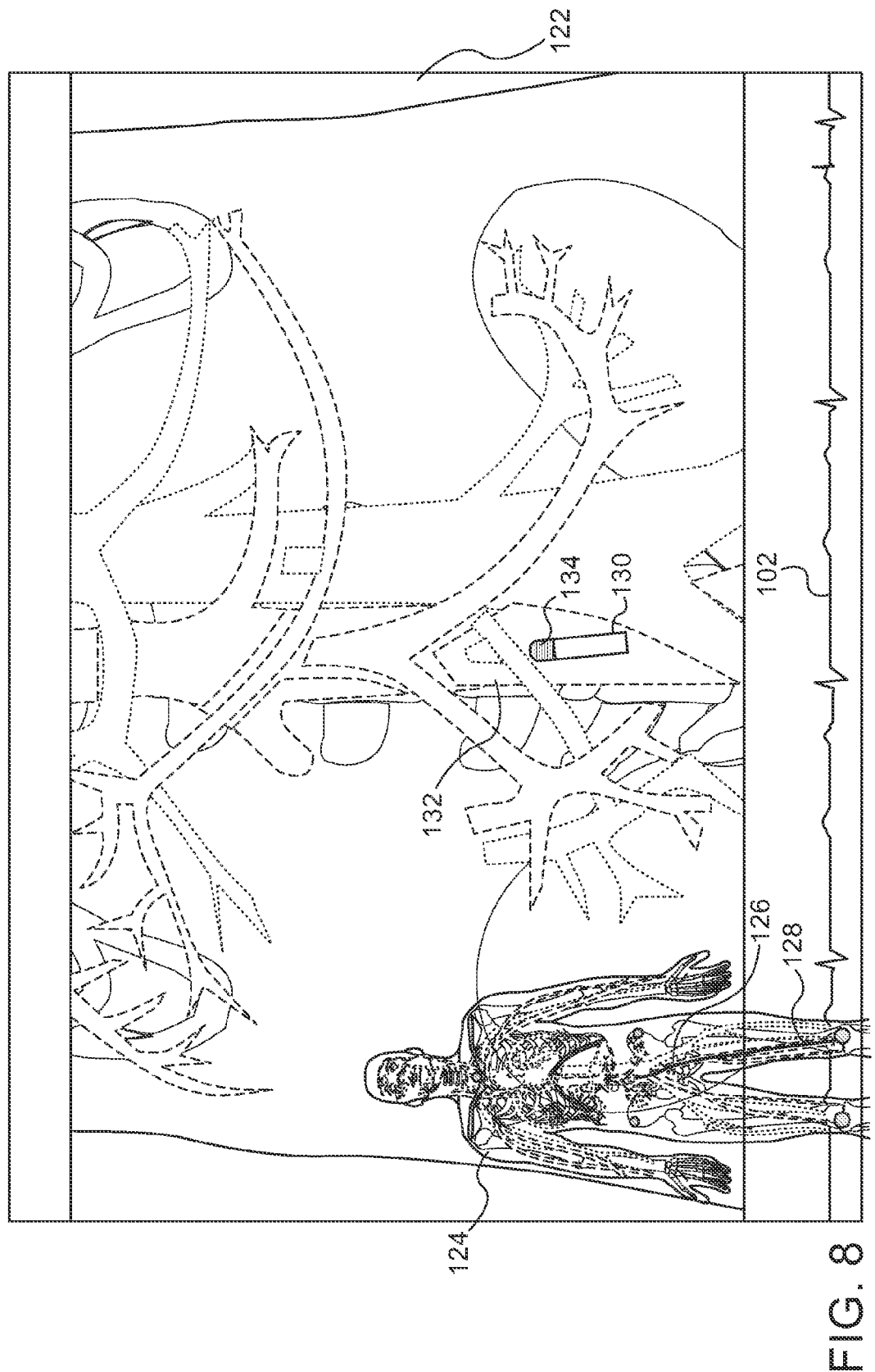
FIG. 8 is a screen display of a skeletal model in accordance with an embodiment of the invention.

Reference is now made to FIG. 8, which is a screen display 122 of a skeletal model, in accordance with an embodiment of the invention. Patient-specific model 124 is shown at the lower left. A sheath 126 for catheter 128 has been inserted using an approach via the left femoral vein. An enlarged display of the abdominal area of the model 124 dominates the screen display 122 and includes an icon 130 representing the distal end of the catheter 128, which is located in inferior vena cava 132. The distal end of the catheter 128 may include a mapping electrode 134, as shown on the icon 130

Figure 9:
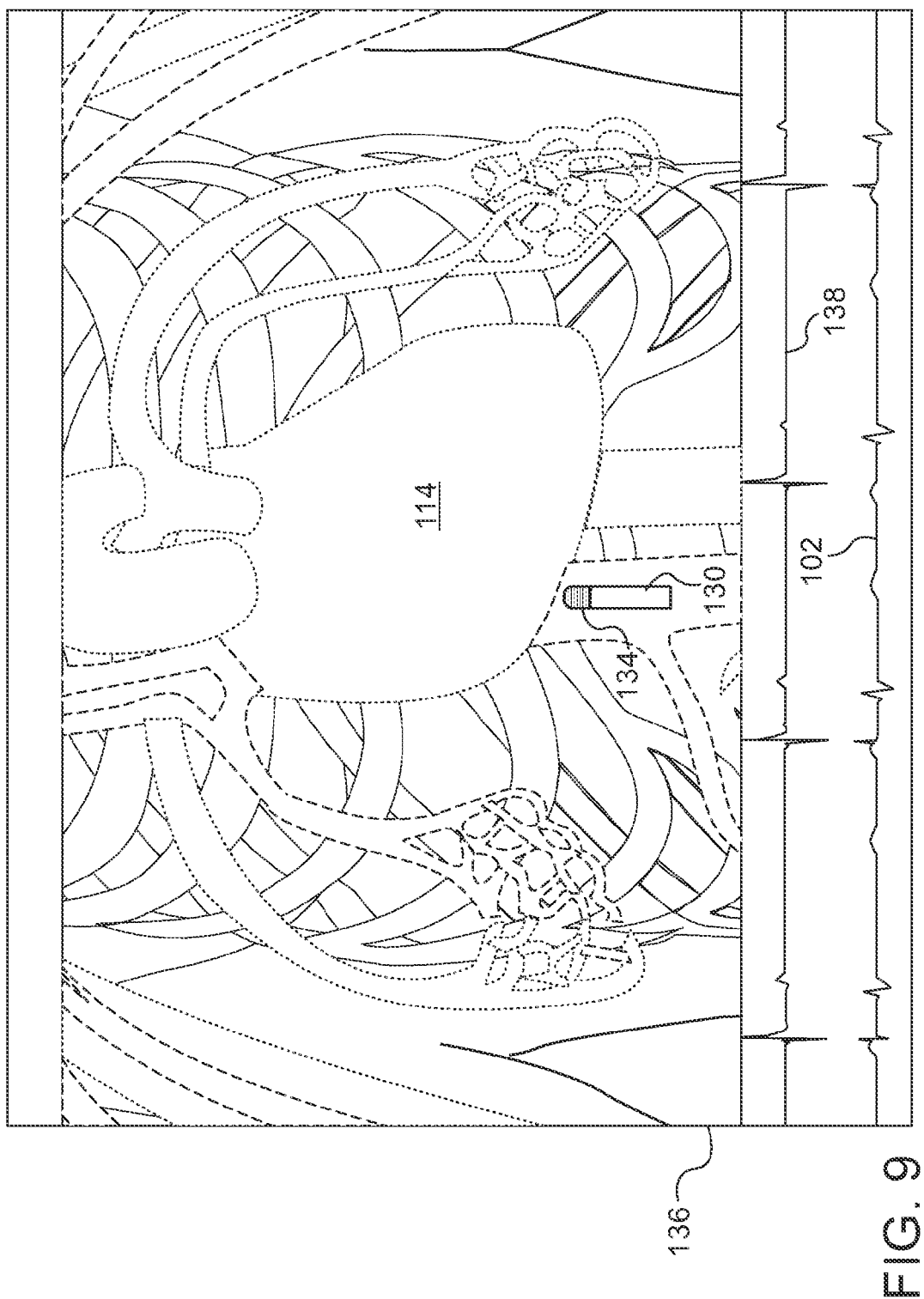
FIG. 9 is a screen display of the thoracic region of the model shown in FIG. 8, in accordance with an embodiment of the invention.

Reference is now made to FIG. 9, which is a screen display 136 of the thoracic region of the model 124 (FIG. 8), in accordance with an embodiment of the invention, showing a progression of the catheterization procedure depicted in FIG. 8. The catheter 128 (FIG. 8) has advanced into the thorax, and is about to enter the right atrium of the heart 114. The mapping electrode 134 at the distal end of the catheter 128 has sensed electrical activity. This event is reflected by the appearance of a second electrocardiographic tracing 138 on the display 136. The CARTO system recognizes the event, and identifies the position of the mapping electrode 134 as the inferior vena caval-right atrial junction. The model 124 may be automatically adjusted in response to the identification of this landmark, in order to more accurately represent the patient's anatomy.

In like manner, in procedures in which the catheter would be introduced through the superior vena cava, appearance of the tracing 138 would signify that the mapping electrode 134 has reached the superior vena caval-right atrial junction.

The movements of the catheter 128 shown in FIG. 8 and FIG. 9 are tracked using information provided by the ACL subsystem as enhanced by the addition of location pads as described herein. The information provided by the ACL subsystem is also processed in other modules of the system 10 (FIG. 1), for example by elements of the CARTO system. The information is sufficiently accurate to within 1-3 mm, which is sufficient to guide the operator in passing the catheter into the heart using the ACL subsystem without recourse to other imaging modalities, e.g., fluoroscopy, magnetic resonance imaging (MRI), or echography. For example, the ACL subsystem as enhanced herein enables deviation of the catheter into a tributary vessel to be detected by the operator or automatically detected. In the latter case the system 10 would alert the operator.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:
1. A method of catheterization, comprising the steps of:
creating a subject-specific skeletal model of a body of a subject;
in the model defining an intended path of a probe within the body that leads from a point of insertion of the probe to a target;
inserting the probe into the body, wherein the probe comprises at least one electrode;
passing electrical currents through the body between the at least one electrode and respective electroconductive location pads that are disposed at a plurality of locations on a surface of the body, wherein the plurality of locations are distributed along the intended path of the probe, the location pads having operating volumes, the location pads being deliberately arranged so that the operating volumes of immediately neighboring pads overlap;
measuring respective characteristics of the currents passing through the plurality of locations; and
while inserting the probe iteratively determining position coordinates of the probe responsively to the measured characteristics;
in the model tracking an actual path of the probe using the iteratively determined position coordinates; and determining whether the actual path corresponds to the intended path, wherein creating a subject-specific skeletal model comprises:
applying a hand-held probe to respective landmarks on the body, the hand-held probe comprising a magnetic sensor;
applying a magnetic field to the magnetic sensor;
receiving signals from the magnetic sensor responsively to the magnetic field;
computing respective positions of the landmarks responsively to the signals; and
including the positions of the landmarks as reference locations in the model, wherein at least one of the conductive pads is a multi-location pad having a plurality of location pad units,
wherein all the location pads are connected to an enhanced active current location (ACL) system,
wherein a respective set of calibration currents is generated between the at least one electrode and the catheter at different positions in a region of interest,
wherein a respective relation is derived for each position between the respective set of the calibration currents and the different positions, and is used in determining the location of the probe in response to the different respective relations and probe currents
wherein, during insertion of the probe, the ACL subsystem processes data derived from selected location pad units, wherein said selected location pad units are those whose operating volumes include or are proximate the current location of the distal end of the probe and wherein distant pad units are ignored,
wherein accuracy of the ACL subsystem is enhanced by correlating impedance measurements taken from the multi-location pad with location information provided by the magnetic sensor, and
wherein the ACL subsystem is calibrated to conform to the position as computed from data supplied by the magnetic sensor.

2. The method according to claim 1, wherein the location pads are spaced apart at intervals between 20 and 40 mm.

3. The method according to claim 1, wherein the at least one electrode comprises a plurality of electrodes, and wherein passing electrical currents comprises passing each of the currents between one of the plurality of electrodes and one of the plurality of locations on the surface of the body.

4. The method according to claim 1, wherein passing electrical currents comprises affixing conductive pads in galvanic contact with the body at the plurality of locations, and passing electrical currents through the conductive pads.

5. The method according to claim 1, wherein tracking an actual path of the probe is performed exclusively using the iteratively determined position coordinates.

6. The method according to claim 1, wherein tracking an actual path of the probe is performed while avoiding imaging the body using another imaging modality.

7. The method according to claim 1, wherein the plurality of locations are relatively densely arranged near the target and more sparsely arranged elsewhere along the intended path of the probe.

8. The method according to claim 1, wherein the probe comprises a magnetic sensor, further comprising the steps of:
calculating additional position coordinates from signals produced by the magnetic sensor;
determining a correlation between the position coordinates with the additional position coordinates; and
refining the position coordinates responsively to the correlation.

9. An apparatus for position sensing, comprising:
a probe, comprising at least one probe electrode, which is adapted to be inserted into a body of a subject;
a plurality of body surface electrodes, which are adapted to be fixed to a surface of the body at respective locations; and
a controller, which is adapted to be coupled to the probe and to the body surface electrodes for passing electrical currents through the body between the at least one probe electrode and the plurality of body surface electrodes, and to iteratively determine position coordinates of the probe by measuring respective characteristics of the currents passing through the plurality of body surface electrodes; and
a processor, operative to perform the steps of:
creating a subject-specific skeletal model of the body;
in the model defining an intended path of the probe within the body that leads from a point of insertion of the probe to a target;
tracking in the model an actual path of the probe during insertion thereof using the iteratively determined position coordinates; and
determining whether the actual path corresponds to the intended path; and
a hand-held probe comprising a magnetic sensor, wherein the processor is operative, when the probe is applied to respective landmarks on the body, to perform the steps of:
applying a magnetic field to the magnetic sensor;
receiving signals from the magnetic sensor responsively to the magnetic field;
computing respective positions of the landmarks responsively to the signals; and
including the positions of the landmarks as reference locations in the model,
wherein the body surface electrodes comprise a multi-location pad having a plurality of location pad units adapted for galvanic contact with the body of the subject, and
wherein the location pad units have operating volumes, the location pads units being deliberately arranged so that the operating volumes of immediately neighboring location pad units overlap,
wherein at least one of the body surface electrodes comprises a multi-location pad having a plurality of location pad units,
wherein all the location pads are connected to an enhanced active current location (ACL) system,
wherein, as respective characteristics of currents passing between the probe and the electrodes of the ACL subsystem are measured, the ACL system is adapted to determine position coordinates of the probe responsively to the measured characteristics,
wherein the ACL subsystem is adapted to generate a respective set of calibration currents between the at least one electrode and the catheter at different positions in a region of interest,
wherein the ACL subsystem is adapted to derive a respective relation for each position between the respective set of the calibration currents and the different positions, and use the derived respective relation in determining the location of the probe in response to the different respective relations and probe currents
wherein, during insertion of the probe, the ACL subsystem processes data derived from selected location pad units, wherein said selected location pad units are those whose operating volumes include or are proximate the current location of the distal end of the probe and wherein distant pad units are ignored, wherein accuracy of the ACL subsystem is enhanced by correlating impedance measurements taken from the multi-location pad with location information provided by the magnetic sensor, and wherein the ACL subsystem is calibrated to conform to the position as computed from data supplied by the magnetic sensor.

10. The apparatus according to claim 9, wherein the at least one probe electrode comprises a plurality of electrodes, and wherein passing electrical currents comprises passing each of the currents between one of the plurality of electrodes and selected ones of the plurality of body surface electrodes.

11. The apparatus according to claim 9, further comprising:
- a magnetic sensor disposed in the probe, wherein the processor is operative to perform the steps of:
- calculating additional position coordinates from signals produced by the magnetic sensor;
- determining a correlation between the position coordinates with the additional position coordinates; and
- refining the position coordinates responsively to the correlation.

12. The apparatus according to claim 9, wherein the location pad units are spaced apart at intervals between 20 and 40 mm.

13. The apparatus according to claim 9, wherein the location pad units are relatively densely arranged near the target and more sparsely arranged elsewhere along the intended path of the probe.

* * * * *